US006262304B1

(12) United States Patent
Hashimoto et al.

(10) Patent No.: US 6,262,304 B1
(45) Date of Patent: Jul. 17, 2001

(54) PROCESS FOR PRODUCING DIMETHYLCYANAMIDE

(75) Inventors: Toshihiro Hashimoto; Takashi Motoi, both of Ibaraki-ken (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 09/630,141

(22) Filed: Jul. 31, 2000

(30) Foreign Application Priority Data

Jul. 29, 1999 (JP) .................................................. 11-214945

(51) Int. Cl.[7] .................................................. C07C 277/08
(52) U.S. Cl. ........................................... 564/232; 564/278
(58) Field of Search ...................................... 564/278, 232

(56) References Cited

FOREIGN PATENT DOCUMENTS

| 1 267 318 | 3/1972 | (GB) . |
| 55-133352 | 10/1980 | (JP) . |
| 61-280463 | 12/1986 | (JP) . |

*Primary Examiner*—Johann Richter
*Assistant Examiner*—Brian J. Davis
(74) *Attorney, Agent, or Firm*—Antonelli, Terry, Stout & Kraus, LLP

(57) ABSTRACT

Cyanogen chloride and dimethylamine are reacted in a water/organic solvent system. The organic solvent is immiscible with water. After the completion of reaction, the water-immiscible organic solvent is distilled away from the reaction product solution to carry out the subsequent synthesis of 1,1,3,3-tetramethylguanidine in an aqueous system.

13 Claims, No Drawings

PROCESS FOR PRODUCING DIMETHYLCYANAMIDE

BACKGROUND OF THE INVENTION

1. Field of the Invention

The present invention relates to a process for producing 1,1,3,3-tetramethylguanidine which is useful as intermediates or raw materials for manufacturing medicines and chemical products, and also relates to a process for producing dimethylcyanamide which is important as the intermediate for 1,1,3,3-tetramethylguanidine.

2. Description of the Prior Art

It is known that dimethylcyanamide can be produced by reacting cyanogen chloride with dimethylamine in an organic solvent which is immiscible with water (British Patent No. 1267318), by reacting cyanogen halide with dimethylamine in an aqueous solvent (Japanese Patent Application Laid-Open No. 55-133352), or by treating sodium or potassium cyanide and dimethylamine with chlorine in an aqueous solvent (Japanese Patent Application Laid-Open No. 61-280463). The dimethylcyanamide thus obtained is used as an intermediate for the synthesis of 1,1,3,3-tetramethylguanidine. 1,1,3,3-Tetramethylguanidine has been produced by reacting dimethylcyanamide with dimethylamine hydrochloride in a water-immiscible organic solvent at high temperature under pressure (British Patent No. 1267318), or by reacting dimethylcyanamide with dimethylamine and dimethylamine hydrochloride in an aqueous solvent (Japanese Patent Application Laid-Open Nos. 61-280463 and No. 55-133352).

A method of producing 1,1,3,3-tetramethylguanidine from dimethylcyanamide in a water-immiscible organic solvent generally involves several problems. The method requires a complicated reaction apparatus because the reaction is carried out at high temperatures under pressure. The reaction conditions are corrosive to the reaction apparatus. Further, the method does not produce 1,1,3,3-tetramethylguanidine in satisfactory yields. In consequence, 1,1,3,3-tetramethylguanidine is produced from dimethylcyanamide preferably in an aqueous solvent as taught by Japanese Patent Application Laid-Open No. 55-133352.

Therefore, the method of British Patent No. 1267318, in which dimethylcyanamide is produced in a water-immiscible organic solvent, is unsuitable because solid matters such as dimethylamine hydrochloride are precipitated during the reaction and the water-immiscible organic solvent must be changed to an aqueous solvent in the subsequent synthesis of 1,1,3,3-tetramethylguanidine in an aqueous solvent.

A method of mixing an aqueous solution of cyanogen chloride with an aqueous solution of dimethylamine is also unsatisfactory in the yields as described in Comparative Example 1. Japanese Patent Application Laid-Open No. 55-133352 discloses in Example 3 that the final yield of 1,1,3,3-tetramethylguanidine amounts to 85.1 mol % by feeding a cyanogen chloride gas into an aqueous solution of dimethylamine. The low yield of 1,1,3,3-tetramethylguanidine of the proposed method would be attributable mainly to a low yield of dimethylcyanamide intermediate.

The method of Japanese Patent Application Laid-Open No. 61-280463 is favorable for producing 1,1,3,3-tetramethylguanidine in an aqueous solvent because dimethylcyanamide is obtained as an aqueous solution. However, the reaction procedures are complicated because chlorine as an oxidant should be blown into a solution containing a reductive organic compound. Further, as described below, the results of applicants' replication of the proposed reaction procedures showed that the reaction involved possible danger of causing fire.

Therefore, an object of the present invention is to provide a simple process for producing dimethylcyanamide safely in high yields. Another object of the present invention is to provide a simple process for producing 1,1,3,3-tetramethylguanidine safely in high yields via dimethylcyanamide.

SUMMARY OF THE INVENTION

All the reported methods for producing dimethylcyanamide by reacting cyanogen chloride with dimethylamine in the presence of water have failed to produce dimethylcyanamide in high yields due to side reactions of cyanogen chloride. Only capable of producing dimethylcyanamide in relatively high yields even in the presence of water is the method disclosed in Japanese Patent Application Laid-Open No. 61-280463. However, as mentioned above, the proposed method requires complicated and strictly controlled procedures such as the blowing of chlorine under strictly controlled pH. Thus, any known methods for the production of dimethylcyanamide inevitably involve drawbacks such as low yield and complicated procedures.

The inventors have now found that dimethylcyanamide is safely produced in high yields by mixing a solution of cyanogen chloride in an organic solvent which is immiscible with water and an aqueous solution of dimethylamine to allow cyanogen chloride to react with dimethylamine. It has been further found that the dimethylcyanamide produced by the above method is free from precipitated solid matters, thereby facilitating the subsequent treatments. In addition, it has been found that the above method does not require complicated procedure and strict control.

Thus, in a first aspect of the present invention, there is provided a process for producing dimethylcyanamide, comprising a step of mixing a solution of cyanogen chloride in an organic solvent which is immiscible with water and an aqueous solution of dimethylamine, thereby allowing cyanogen chloride to react with dimethylamine.

The reaction product solution containing dimethylamine obtained in the above process is used as a raw material for producing 1,1,3,3-tetramethylguanidine after simple procedure of removing the organic solvent by distillation. By adding dimethylamine to a solution after removing the organic solvent and heating, 1,1,3,3-tetramethylguanidine hydrochloride is easily synthesized. Free 1,1,3,3-tetramethylguanidine is recovered by neutralizing hydrogen chloride with alkali such as sodium hydroxide and potassium hydroxide, and treating the resulting solution with usual methods such as extraction, salting out and distillation.

Thus, in a second aspect of the present invention, there is provided a process for producing 1,1,3,3-tetramethylguanidine, comprising a step of mixing a solution of cyanogen chloride in an organic solvent which is immiscible with water and an aqueous solution of dimethylamine to allow cyanogen chloride to react with dimethylamine, thereby obtaining a dimethylcyanamide solution; a step of removing the organic solvent from the dimethylcyanamide solution by distillation; and a step of heating the resulting solution after adding dimethylamine.

DETAILED DESCRIPTION OF THE INVENTION

In the process of the present invention, one mole of cyanogen chloride is reacted with one mole of dimethylamine to produce one mole of dimethylcyanamide together with hydrogen chloride. To neutralize the generated hydrogen chloride, one mole of a base such as sodium hydroxide and dimethylamine is required, thereby producing one mol of a hydrochloride of the base. Since dimethylamine is generally used as the base, 2 moles of dimethylamine is added per one mole of cyanogen chloride to complete the reaction.

Cyanogen chloride and dimethylamine may be used in another molar ratio other than the above. An excess portion remains unreacted in the reaction product solution. Therefore, the use of excess dimethylamine is preferred to prevent cyanogen chloride from remaining unreacted, because care must be taken in handling a reaction product solution containing the remaining cyanogen chloride due to its high toxicity and corrosive properties. However, the use of a large excess dimethylamine is disadvantageous, because the remaining dimethylamine is distilled together with the organic solvent during the distillation prior to the subsequent synthesis of 1,1,3,3-tetramethylguanidine, thereby requiring an additional step for separating dimethylamine from the organic solvent. Therefore, the amount of dimethylamine to be used is preferably about 2 to 2.2 moles per one mole of cyanogen chloride.

The solution of cyanogen chloride in water-immiscible organic solvent may be mixed with the aqueous solution of dimethylamine by any of the following manners:

(a) adding, preferably dropwise, the solution of cyanogen chloride in water-immiscible organic solvent to the aqueous solution of dimethylamine;
(b) feeding the solution of cyanogen chloride in water-immiscible organic solvent simultaneously with the aqueous solution of dimethylamine into a flow reactor in an amount ratio of completing the reaction; and
(c) adding, preferably dropwise, the aqueous solution of dimethylamine to the solution of cyanogen chloride in water-immiscible organic solvent.

The concentration of the solution of cyanogen chloride in water-immiscible organic solvent is preferably 10 to 30% by weight, and the concentration of the aqueous solution of dimethylamine is preferably 20 to 60% by weight, although not strictly limited thereto.

Since excessively high reaction temperatures volatilize cyanogen chloride or dimethylamine, or cause side reactions, the reaction temperature is preferably 50° C. or lower, more preferably 0 to 30° C. The reaction between cyanogen chloride and dimethylamine is completed immediately after mixing. Therefore, the reaction time usually depends on the addition speed (dropping speed) and/or the amounts of the reactants.

The water-immiscible organic solvent used for dissolving cyanogen chloride must be removed from the reaction product solution prior to the subsequent synthesis of 1,1,3, 3-tetramethylguanidine. Therefore, a water-immiscible organic solvent having the boiling point lower than that of water is preferably used. Examples of the water-immiscible organic solvents include methylene chloride, chloroform, carbon tetrachloride, benzene and cyclohexane. Methylene chloride is particularly preferred.

The reaction product solution from the reaction of cyanogen chloride and dimethylamine is usually used in the subsequent process for producing 1,1,3,3-tetramethylguanidine without isolating dimethylcyanamide. The dimethylcyanamide formed can be recovered, if necessary, by distillation of the organic solvent layer. A part of the dimethylcyanamide dissolved in the aqueous layer can be recovered by extracting it with an organic solvent as used in dissolving cyanogen chloride and distilling the extract.

1,1,3,3-Tetramethylguanidine hydrochloride is produced using the reaction product solution containing dimethylcyanamide in the manner described below. First, the water-immiscible organic solvent is distilled away from the reaction product solution until the concentration of the water-miscible organic solvent is reduced to 1% by weight or lower. After adding an amount of dimethylamine, the reaction product solution thus treated is heated at 60 to 100° C. for 3 to 10 hours preferably around atmospheric pressure. The addition amount of dimethylamine is preferably 0.05 to 1.5 moles, more preferably 0.1 to 1 mole per one mole of dimethylcyanamide.

The 1,1,3,3-Tetramethylguanidine hydrochloride formed can be recovered in a manner known in the art, for example, by evaporating water. It can be purified by recrystallization using, for example, alcoholic solvent. To recover free 1,1, 3,3-tetramethylguanidine, an alkaline solution such as an aqueous sodium hydroxide solution is added to the reaction product mixture to liberate the free 1,1,3,3-tetramethylguanidine which is then extracted by an organic solvent such as toluene.

The present invention will be described in more detail by the following examples. However, it should be noted that the scope of the present invention is not intended to limit thereto.

EXAMPLE 1

A glass reactor equipped with a dropping funnel and a reflux condenser was charged with 29.8 g of dimethylamine and 29.8 g of water. While stirring by a magnetic stirrer, a solution of 20.4 g of cyanogen chloride in 81.5 g of methylene chloride was added dropwise into the reactor through the dropping funnel over about one hour. The reactor was cooled in an ice water bath to maintain the reaction temperature at 15 to 20° C.

The reaction product solution after completion of the dropwise addition was in clear, colorless two layers without precipitation of solid matters. The methylene chloride layer was separated from the reaction product solution, and the remaining water layer was extracted with 20 g of methylene chloride. Gas chromatographic analysis of the collected organic layers showed that the yield of dimethylcyanamide was 98.2 mol % based on cyanogen chloride used.

EXAMPLE 2

The same procedures as in Example 1 were repeated except that the reaction temperature was changed to 40 to 45° C., thereby obtaining dimethylcyanamide in 96.8 mol % yield.

EXAMPLE 3

A solution of 20.4 g of cyanogen chloride in 81.5 g of methylene chloride and a solution of 29.8 g of dimethylamine in 29.8 g of water were separately fed into a 3-ml overflow reactor over about one hour under stirring by a magnetic stirrer. The feeding rates of the respective solutions were controlled so as to regulate the pH of the overflowing liquid within the range of 6 to 8. The reactor was cooled in an ice water bath to maintain the reaction temperature at 15 to 20° C. The overflowed liquid was separated and analyzed in the same manner as in Example 1. The results showed that the yield of dimethylcyanamide was 98.9 mol %.

Comparative Example 1

A glass reactor equipped with a reflux condenser and an inlet for pumping a solution of cyanogen chloride was charged with 29.8 g of dimethylamine and 29.8 g of water. While stirring by a magnetic stirrer, a mixed solution containing 20.4 g of cyanogen chloride, 81.5 g of water and one drop of 36% hydrochloric acid was pumped into the reactor over about one hour. Since the mixture was in two separated layers due to liberation of a part of cyanogen chloride, the mixture was vigorously stirred during storage and then pumped into the reactor in the form of a suspension. The reactor was cooled in an ice water bath to maintain the reaction temperature at 15 to 20° C.

The reaction product solution after the completion of dropwise addition of the mixture was clear and colorless without precipitation of solid matters. The reaction product solution was extracted twice with 50 g of methylene chloride. Gas chromatographic analysis of the collected organic phase showed that the yield of dimethylcyanamide was 72.1 mol % based on the cyanogen chloride used.

Reference Example 1

Into a glass reactor equipped with an inlet for raw materials, a glass inlet tube for chlorine which was disposed so that its end submerged below the liquid surface, a pH meter and a reflux condenser, was charged 40 g of water. While stirring with a magnetic stirrer, a mixture of 63.7 g of sodium cyanide, 122.9 g of dimethylamine and 186.6 g of water was fed into the reactor at a feeding rate of 4 to 5 ml/min. Simultaneously, chlorine was fed into the reaction liquid system through the chlorine inlet tube while regulating the reaction solution within pH 7 to 9. The reactor was cooled in an ice water bath to maintain the reaction temperature at 15 to 20° C.

About 20 minutes after the start of reaction (after feeding about 120 g of the mixture), a spark-like phenomenon was observed at the end portion of the chlorine inlet tube, and the liquid was colored slightly yellow. The spark-like phenomenon was observed twice in repeating the experiment ten times. The conditions for causing the spark-like phenomenon were not elucidated.

EXAMPLE 4

In the same manner as in Example 1, dimethylcyanamide was obtained in 98.5 mol % yield based on cyanogen chloride. From the reaction product solution containing 0.327 mol of dimethylcyanamide, methylene chloride was distilled away under reduced pressure to lower its concentration to 0.3% by weight of the total liquid.

After adding 29.9 g of 50% by weight aqueous solution of dimethylamine (0.332 mol of dimethylamine), the resulting solution was heated at 70° C. for five hours under stirring by a magnetic stirrer in a glass reactor equipped with a reflux condenser. After the completion of reaction, the reaction product solution was added with 83.8 g of 40% by weight aqueous sodium hydroxide and extracted with 100 g of toluene. The results of gas chromatographic analysis on the extract showed that 1,1,3,3-tetramethylguanidine was produced in 98.3 mol % yield based on dimethylcyanamide.

EXAMPLE 5

In the same manner as in Example 1, dimethylcyanamide was obtained in 98.7 mol % yield based on cyanogen chloride. From the reaction product solution containing 0.328 mol of dimethylcyanamide, methylene chloride was distilled away under reduced pressure to lower its concentration to 0.3% by weight of the total liquid.

After adding 6.0 g of 50% by weight aqueous solution containing 0.332 mol of dimethylamine, the resulting solution was heated at 95° C. for five hours under stirring by a magnetic stirrer in a glass reactor equipped with a reflux condenser. After the completion of reaction, the reaction product solution was added with 75.2 g of 40% by weight aqueous sodium hydroxide and extracted with 100 g of toluene. The results of gas chromatographic analysis on the extract showed that 1,1,3,3-tetramethylguanidine was produced in 96.7 mol % yield based on dimethylcyanamide.

As described in detail, according to the present invention, dimethylcyanamide and its derivative of 1,1,3,3-tetramethylguanidine are produced in high yields in safe and simple manners.

What is claimed is:

1. A process for producing dimethylcyanamide, comprising a step of mixing a solution of cyanogen chloride in an organic solvent which is immiscible with water and an aqueous solution of dimethylamine, thereby allowing cyanogen chloride to react with dimethylamine.

2. The process according to claim 1, wherein said organic solvent which is immiscible with water is at least one solvent selected from the group consisting of methylene chloride, chloroform, carbon tetrachloride, benzene and cyclohexane.

3. The process according to claim 1, wherein said organic solvent which is immiscible with water is methylene chloride.

4. The process according to claim 1, wherein the reaction is carried out at 50° C. or lower.

5. The process according to claim 1, wherein 2 to 2.2 moles of dimethylamine is used per one mole of cyanogen chloride.

6. A process for producing 1,1,3,3-tetramethylguanidine, comprising:
   a first step of mixing a solution of cyanogen chloride in an organic solvent which is immiscible with water and an aqueous solution of dimethylamine to allow cyanogen chloride to react with dimethylamine, thereby obtaining a dimethylcyanamide solution;
   a second step of removing the organic solvent from the dimethylcyanamide solution by distillation; and
   a third step of adding dimethylamine and heating the resulting solution.

7. The process according to claim 6, wherein said organic solvent which is immiscible with water is at least one solvent selected from the group consisting of methylene chloride, chloroform, carbon tetrachloride, benzene and cyclohexane.

8. The process according to claim 6, wherein said organic solvent which is immiscible with water is methylene chloride.

9. The process according to claim 6, wherein the reaction of the first step is carried out at 50° C. or lower.

10. The process according to claim 6, wherein 2 to 2.2 moles of dimethylamine is used per one mole of cyanogen chloride.

11. The process according to claim 6, wherein the organic solvent is removed until the concentration thereof reaches 1% by weight or lower.

12. The process according to claim 6, wherein 0.05 to 1.5 moles of dimethylamine per one mole of dimethylcyanamide is added in the third step.

13. The process according to claim 6, wherein the heating of the third step is carried out at 60 to 100° C. for 3 to 10 hours.

* * * * *